United States Patent
Gilreath et al.

(10) Patent No.: US 12,245,990 B2
(45) Date of Patent: Mar. 11, 2025

(54) PORTABLE MEDICATION CONTAINER

(71) Applicant: Evernorth Strategic Development, Inc., St. Louis, MO (US)

(72) Inventors: Lindsay N. Gilreath, Edwardsville, IL (US); Robert E. Hoffman, Linden, IN (US)

(73) Assignee: Evernorth Strategic Development, Inc., St. Louis, MO (US)

(*) Notice: Subject to any disclaimer, the term of this patent is extended or adjusted under 35 U.S.C. 154(b) by 347 days.

(21) Appl. No.: 17/727,274

(22) Filed: Apr. 22, 2022

(65) Prior Publication Data

US 2022/0339071 A1    Oct. 27, 2022

Related U.S. Application Data

(60) Provisional application No. 63/178,393, filed on Apr. 22, 2021.

(51) Int. Cl.

| | |
|---|---|
| *A61J 7/04* | (2006.01) |
| *A61J 1/03* | (2023.01) |
| *A61J 7/00* | (2006.01) |
| *G16H 20/13* | (2018.01) |

(52) U.S. Cl.
CPC .............. *A61J 7/0436* (2015.05); *A61J 1/03* (2013.01); *A61J 7/0076* (2013.01); *A61J 7/0418* (2015.05); *G16H 20/13* (2018.01); *A61J 2200/30* (2013.01); *A61J 2200/70* (2013.01); *A61J 2200/74* (2013.01); *A61J 2205/60* (2013.01)

(58) Field of Classification Search
CPC .......... A61J 7/0436; A61J 7/0418; A61J 1/03; A61J 7/0076; G16H 20/13; B65D 83/0409; B65D 51/248

USPC .......................................................... 221/1
See application file for complete search history.

(56) References Cited

U.S. PATENT DOCUMENTS

| | | |
|---|---|---|
| 6,382,416 B1 | 5/2002 | Gainey |
| 8,261,939 B2 | 9/2012 | Knoth |
| 8,322,528 B2 | 12/2012 | Sterns |

(Continued)

FOREIGN PATENT DOCUMENTS

| | | | |
|---|---|---|---|
| CN | 117012329 A | * | 11/2023 |
| JP | 56767552 A | | 8/2013 |

OTHER PUBLICATIONS

Hoffman, U.S. Appl. No. 17/122,656—Cap Assembly for a Medication Container, filed Dec. 15, 2020.
Icebreakers, photo of packaging, as early as Jan. 1, 2019.

*Primary Examiner* — Luna Champagne
(74) *Attorney, Agent, or Firm* — Dickinson Wright PLLC

(57) ABSTRACT

The medication container includes a generally card-shaped housing with an interior. The housing has a first opening that is sized to allow a plurality of pills to simultaneously be inserted into the interior of the housing and a first door that is movable between an open position and a closed position to selectively open and close the first opening. The housing also has a second opening that is spaced from the first opening and is configured to only allow a single dose of pills to be dispensed at a time. A second door is movable between open and closed positions. Electronic circuitry is disposed in the interior of the housing and is configured to detect the passage of the pills through the second opening and also to record data pertaining to each dispensing event to a memory contained within the interior of the housing.

18 Claims, 7 Drawing Sheets

(56) References Cited

U.S. PATENT DOCUMENTS

| | | |
|---|---|---|
| 8,944,282 B2 | 2/2015 | Kroupa |
| 9,125,798 B2 | 9/2015 | Stein |
| 9,311,452 B2 | 4/2016 | Dickie |
| 9,836,583 B2 | 12/2017 | García et al. |
| 10,392,181 B2 | 8/2019 | Zonana |
| 2004/0056035 A1 | 3/2004 | Baker |
| 2016/0250105 A1 | 9/2016 | Rogers, Jr. |
| 2017/0270274 A1* | 9/2017 | García .................. A61J 7/0084 |
| 2018/0068087 A1 | 3/2018 | García |
| 2018/0085287 A1* | 3/2018 | Kim ...................... G07F 11/165 |
| 2018/0215526 A1* | 8/2018 | Hsu ....................... A61J 7/0076 |
| 2019/0228852 A1 | 7/2019 | García |
| 2019/0365607 A1 | 12/2019 | Kugler |

\* cited by examiner

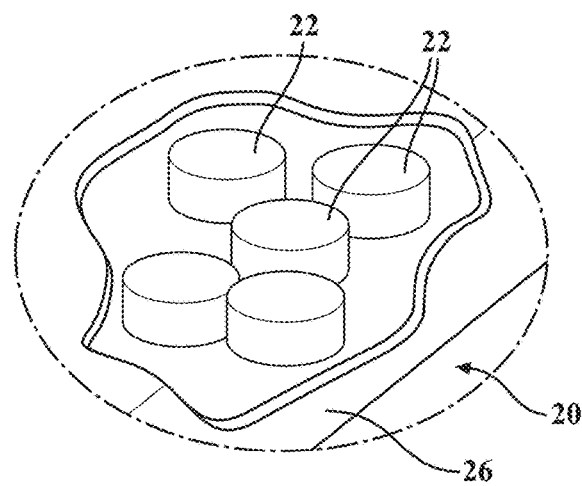
FIG. 4
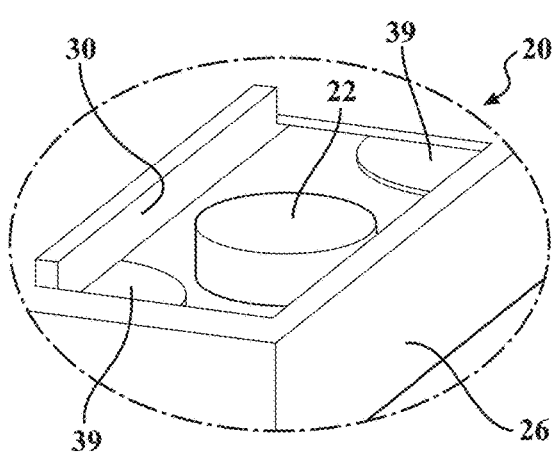
FIG. 5
FIG. 6
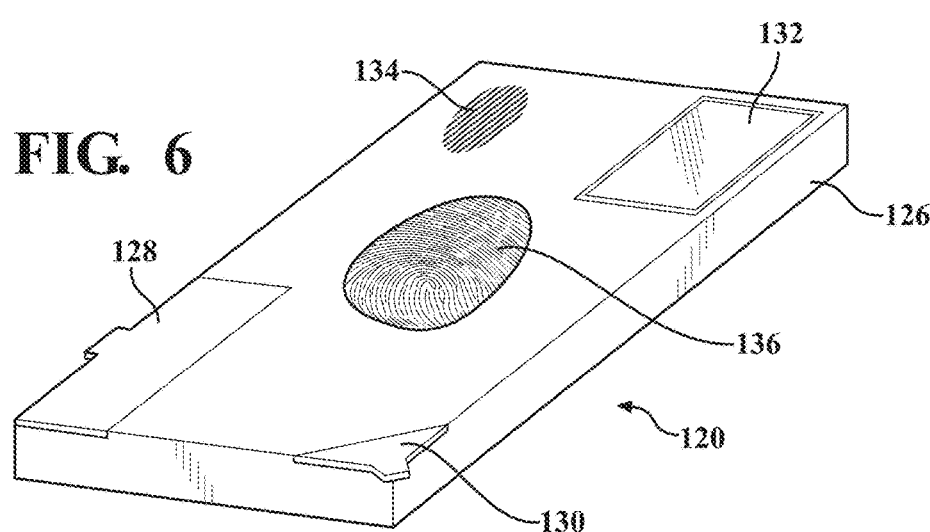
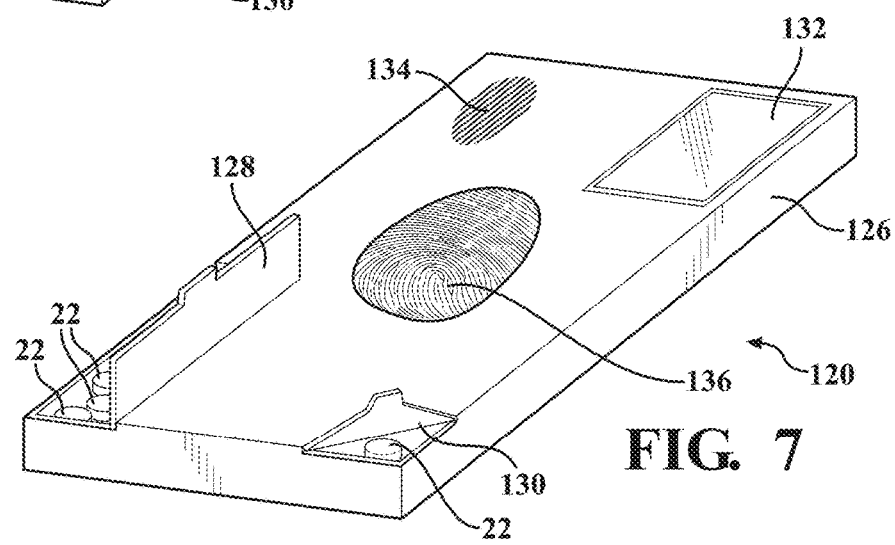
FIG. 7

PORTABLE MEDICATION CONTAINER

CROSS-REFERENCE TO RELATED APPLICATION

This application claims priority to U.S. Provisional Patent Application No. 63/178,393, filed on Apr. 22, 2021, entitled "MEDICATION CONTAINER," the entire contents of which is herein incorporated by reference.

FIELD

The subject disclosure is generally related to medication containers and, more particularly, medication containers of the type that can be filled with a range of different medications and can be conveniently carried by a user so the user can take their medication wherever they are at a designated dosage time.

BACKGROUND

Medication compliance by patients is a known problem in the medical industry because patients often, either intentionally or accidentally, fail to follow a medication regimen prescribed by a medical provider. In some cases, as little as a single missed dose may require a patient to restart a medication regimen from the beginning. One known product which seeks to improve medication compliance, includes a plurality of packets, each of which contains only the medications that the user has to take at a certain time. In other words, the pills are divided, not by type, but by when they should be taken. However, there remains a continuing need for a product that is can improve medication compliance and which is both more convenient and less costly than other known solutions.

SUMMARY

One aspect of the present disclosure is related to a medication container that includes a generally card-shaped housing with an interior that is able to hold a plurality of pills. The housing has a first opening that is sized to allow a plurality of pills to simultaneously be inserted into the interior of the housing and a first door that is movable between an open position and a closed position to selectively open and close the first opening. The housing also has a second opening that is spaced from the first opening and is configured to only allow a single dose of pills to be dispensed from the interior of the housing at a time. A second door movable between an open position and a closed position to selectively open and close the second opening. Electronic circuitry is disposed in the interior of the housing and is configured to detect the passage of the pills through the second opening and also to record data pertaining to each dispensing event to a memory contained within the interior of the housing.

According to another aspect of the present disclosure, the electronic circuitry includes at least one touchless sensor that is configured to detect the passage of pills through the second opening without contact between the at least one touchless sensor and the pills.

According to yet another aspect of the present disclosure, the at least one touchless sensor includes at least one photoreflective diffuse sensor that is configured to sense a break in a path of light from a light source to a light detector.

According to yet another aspect of the present disclosure, the electronic circuitry includes a wireless module that is able to transmit the data pertaining to each dispensing event from the memory to an external device.

According to still another aspect of the present disclosure, at least one of the first door and the second door is a slidable door that can slide between the open and closed positions.

According to a further aspect of the present disclosure, at least one of the first door and the second door includes a living hinge and can pivot between the open and closed positions.

According to yet a further aspect of the present disclosure, the medication container further includes a door locking device that can lock the second door and only unlock the second door in response to a positive verification that an approved person is requesting the second door to be unlocked.

According to still a further aspect of the present disclosure, the second opening is located at a corner of a top wall of the housing.

According to another aspect of the present disclosure, the housing includes a guide with at least one guide wall that channels the pills in the interior of the housing towards the second opening and singulates the pills such that only a single pill can be aligned with the second opening for dispensing at a time.

According to yet another aspect of the present disclosure, the medication container further includes a weight sensor contained within the interior of the housing and configured to weigh the contents of pills within the interior. The weight sensor is also configured to transmit weight data to the electronic circuitry.

According to still another aspect of the present disclosure, the second door is a dispensing door. The housing further includes a plurality of walls located within the interior of the housing and divides the housing into a plurality of chambers. The housing has a plurality of dispensing doors with each dispensing door is associated with one of the chambers.

Another aspect of the present disclosure is related to a medication container that includes a generally card-shaped housing with an interior that is able to hold a plurality of pills. The housing includes a filling opening that is sized to allow a plurality of pills to simultaneously be inserted into the interior of the housing. A filling door is movable between an open position and a closed position to selectively open and close the filling opening. A dispensing opening is spaced from the first opening and is configured to only allow a single dose of pills to be dispensed from the interior of the housing at a time. A dispensing door is movable between an open position and a closed position to selectively open and close the dispensing opening. A pair of guide walls are positioned within the interior of the housing and converge towards one another in a direction towards the dispensing opening for singulating the pills so that only a single dose of the pills can be aligned with the dispensing opening at a time.

According to another aspect of the present disclosure, the single dose of pills that can be aligned with the dispensing opening at a time includes only a single pill.

According to yet another aspect of the present disclosure, the dispensing opening is located at a corner of a top wall of the housing.

According to still another aspect of the present disclosure, further electronic circuitry is disposed in the interior of the housing and is configured to detect the passage of the pills through the dispensing opening and record data pertaining to each dispensing event to a memory contained within the interior of the housing.

According to a further aspect of the present disclosure, the electronic circuitry includes at least one touchless sensor is configured to detect the passage of pills through the dispensing opening without contact between the at least one touchless sensor and the pills.

According to yet a further aspect of the present disclosure, the at least one touchless sensor includes at least one photoreflective diffuse sensor that is configured to sense a break in a path of light from a light source to a light detector.

According to still a further aspect of the present disclosure, the filling door is slidable between the open and closed positions and wherein the open position includes a plurality of different open positions with different areas of the filling opening being exposed.

According to another aspect of the present disclosure, the housing further includes a plurality of walls located within the interior of the housing and dividing the housing into a plurality of chambers. The housing has a plurality of dispensing doors with each dispensing door being associated with one of the chambers.

Yet another aspect of the present disclosure is related to a medication container that includes a generally card-shaped housing with a planar top and a planar bottom and an interior volume. A plurality of pills are contained within the interior volume. The interior volume has a height that is less than two times a minor dimension of the pills such that the pills cannot stack on top of one another within the interior volume. The housing has a larger filling opening and a smaller dispensing opening. A filling door closes the filling opening and a dispensing door closes the dispensing opening. A pair of guide walls are disposed within the interior volume and converge towards one another in a direction towards the dispensing opening to singulate the pills within the interior volume such that only a single one of the pills can be aligned with the dispensing opening at a time. An electronic locking mechanism selectively locks the dispensing door in a closed position. A biometrics sensor is in electrical communication with the electronic locking mechanism and is configured to only unlock the dispensing door upon a positive verification of a user. A non-contact pill sensor is disposed at the dispensing opening and is configured to detect the dispensing of pills out of the interior volume of the housing. A microprocessor, a memory, and a wireless module are disposed within an electronics chamber within the interior volume of the housing. The microprocessor is configured to record data pertaining to dispensing events into the memory, and the wireless module is configured to communicate the data to an external device.

BRIEF DESCRIPTION OF THE DRAWINGS

These and other features and advantages of the present disclosure will be readily appreciated, as the same becomes better understood by reference to the following detailed description when considered in connection with the accompanying drawings wherein:

FIG. 4 is an enlarged and partially fragmentary view of a portion of FIG. 1 and showing a plurality of pills contained within the medication container;

FIG. 5 is an enlarged view of a portion of FIG. 2 and showing a pill in a ready to dispense position aligned with a dispensing opening;

FIG. 6 is a perspective and elevation view of an alternate embodiment of the medication container;

FIG. 7 is another perspective and elevation view of the medication container of FIG. 6 and showing a dispensing gate and a filling gate both being in open positions;

FIG. 14 is an exploded view of a housing of yet another embodiment of the medication container.

DESCRIPTION OF THE ENABLING EMBODIMENTS

Figure 1:
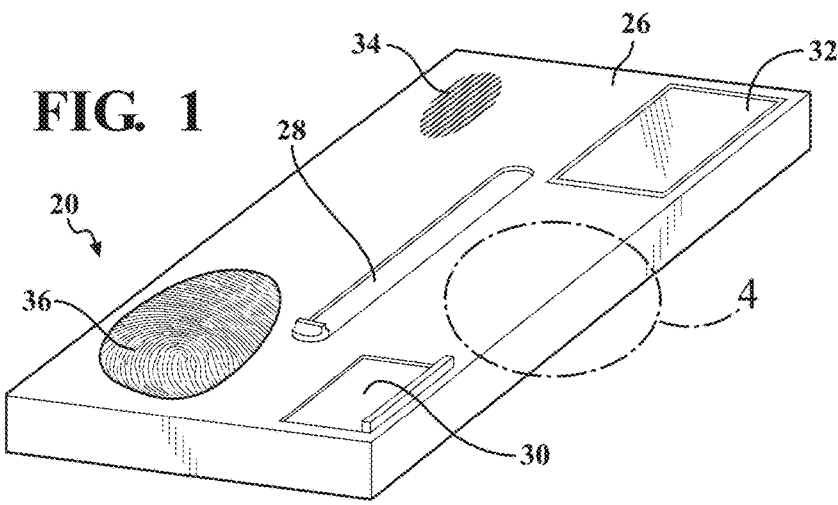
FIG. 1 is a perspective and elevation view of a first exemplary embodiment of a medication container.

Referring to the Figures, wherein like numerals indicate corresponding parts throughout the several views, a first embodiment of an improved medication container 20 is generally shown in FIG. 1-5. As discussed in further detail below, the medication container 20 is a low-cost and highly effective approach to improving a patient's compliance of a medication schedule by controlling and monitoring the dispensing of medications in the form of pills 22. The medication container 20 is configured to be sold as an empty container and filled with any suitable types of pills 22 by the user. The medication container 20 is configured to wirelessly transmit information pertaining to each filling and each dispensing event to at least one external device 24 (shown in FIGS. 13 and 15), such as a computing device, e.g., a smart phone, a computer, a server or the like. The transmission of data relating to dispensing can be sent wirelessly.

The external device 24 may be controlled either by the patient (frequently hereinafter referred to as "user"), by a medical provider, a pharmacy, a pharmacy benefit provider, or combinations thereof. The external device 26 can include a display to display for its user an easy to access log of all dispensing events. Specifically, the log may include time stamps and quantities of pills 22 dispensed or graphics related to pills 22 dispensed from the medication container 20. The graphics can be triggered by a flag value stored in memory for the prescribed dosing regimen for the patient and the medication. Thus, the medication container 20 improves medication compliance (e.g., adherence) by helping the user avoid either missing medication doses, taking medication at the wrong time, or taking double doses of medication. In an embodiment where a medical provider is provided with access to the log of dispensing events, the medical provider may be able to better diagnose or otherwise treat a the user's illness with the full knowledge of how well that user is conforming to their medication schedule. The use of the word pills 22 herein is intended to cover any suitable types of solid medications, including capsules, tablets, or the like.

The medication container 20 includes a housing 26 with a generally cuboid shape that is substantially wider and long than it is tall, i.e., the housing 24 is generally thin. The housing 26 can be generally card-shaped, e.g., thinner in one dimension than the other two dimensions. The housing 26 includes a planar top, a planar bottom, and four side walls that collectively surround an open interior, which defines a solids storage volume. The housing 26 may include a single or multiple pieces of a durable plastic material (or other rigid material, e.g., metal, alloys, polymers, and combinations thereof) and may be shaped through one or more injection molding operations, for example. In the exemplary embodiment, the interior is sized to accommodate a plurality of pills 22 in a loose but not stacked configuration, i.e., only a single row of pills 22 or single high, two-dimensional matrix of pills 22. Thus, a height of the interior space is slightly greater than a thickness or minor dimension of the pills 22 so that the pills 22 can slide within the interior but cannot stack on top of one another. Specifically, the higher of the interior space is less than two times the minor dimension of the pills 22. In some embodiments, the interior may be sized to accommodate more pills 22 than this. For example, in some embodiments, the pills can be stacked on top of one another in a three-dimensional matrix. The loose configuration of the pills, or other solid individual items, stored with the storage volume of the housing allow the pills to freely move within the storage volume. The housing can define a mass storage area within the storage volume and a dispensing channel within the storage volume. The dispensing channel can begin singulating the pills for dispensing. In an example, singulating can be structures and associated operational processes to place the multiple pills in the storage in a manner so that the dispenser operates to dispense a single, individual pill at one time or single action by the dispenser. The housing 26 is preferably small in size so that it can fit in the user's hand or in a pants pocket, thereby allowing it to be very easily transported by the user. In an example, embodiment, the housing 26 has a length dimension in a range of 3.0-5.0 cm, a width dimension of 1.5-3.0 cm, and a height dimension of less than 0.6 cm, +/−0.2 cm. In an example embodiment, the housing 26 is sized to hold at least a single fulfillment of a prescription drugs, e.g., pills, capsules, and the like. A single fulfillment can be seven days, fourteen days, twenty eight days, thirty days, sixty days, ninety days, or similar prescription regime fulfillments.

The housing 26 contains a plurality of electrical components, which are discussed in further detail below, for monitoring the passage of the pills 22 into and out of the interior through at least one passage that can be selectively opened or closed by at least one gate. In an example, the electronic circuitry can detect passage of the pill 22 without contacting the pill 22. In an example, the electronic circuitry can detect the position of the gate, e.g., open, closed or intermediate. Specifically, in the first exemplary embodiment, the housing 26 includes multiple passages, e.g., two passages, which can be selectively opened and closed by two gates or doors, namely, a filling gate 28 or filling door and a dispensing gate 30 or dispensing door. In this embodiment, each of the filling gate 28 and dispensing gate 20 can slide along respective rails, which are formed into a lower surface of the top of the housing 26, between open and closed positions. Each gate 28, 30 includes an upwardly projecting tab that can be gripped, pressed, or otherwise engaged by the user to facilitate this movement between the open position and the closed position, or intermediate positions. Both of the gates 28, 30 are shown in their respective closed positions in FIG. 1. The dispensing gate 30 is shown in its open position in FIGS. 2, 3, and 5. In an example, the aperture in the top wall of the housing 26 covered by the dispensing gate 30 can be dimensioned such that a single pill 22 can pass though the aperture and out of the storage volume of the housing 26. The electronic circuitry can also store data related to the change in state of either gate 28, 30. This information can be correlated to loading pills into the dispenser and/or removing pills from the dispenser. In an example, the action of the gate is correlated to the sensed movement of the pills as detected by the sensors as described herein.

Figure 2:
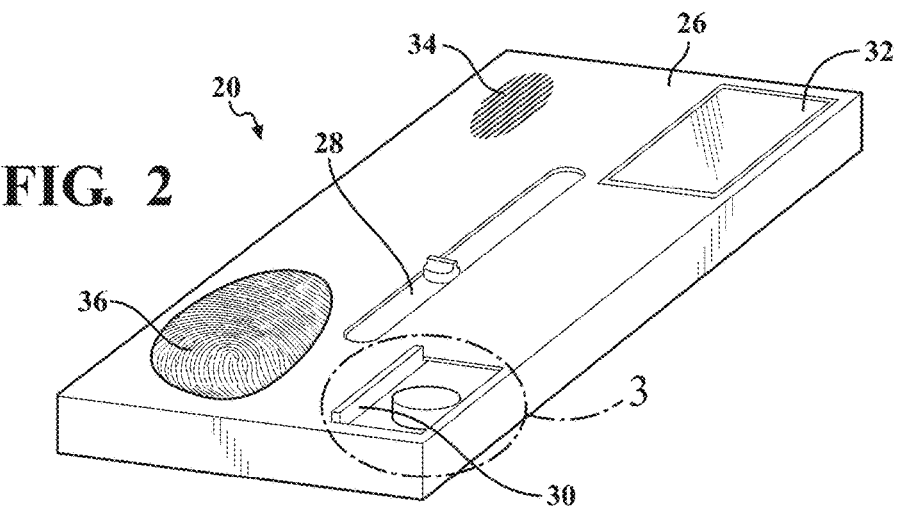
FIG. 2 perspective and elevation view of the medication container of shown in FIG. 1 and showing a dispensing gate in an open position and showing a filling gate in a first open position.
Figure 3:
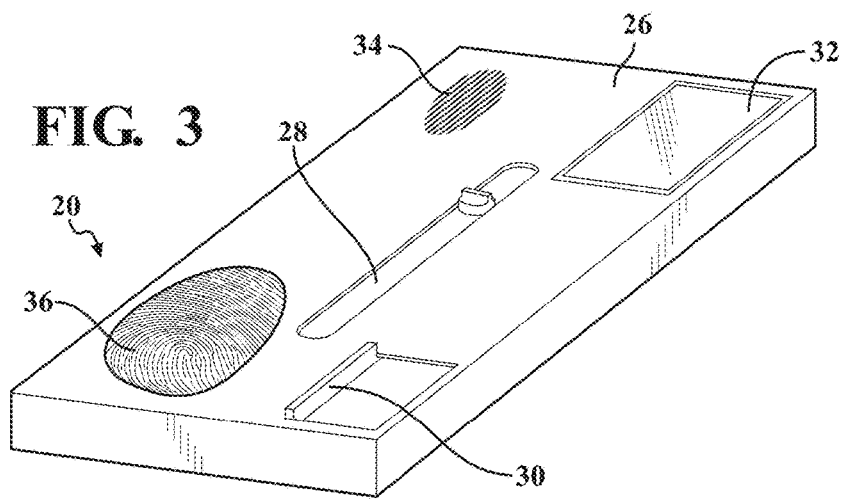
FIG. 3 is another perspective and elevation view of the medication container of FIG. 1 and showing the dispensing gate in the open position and showing the filling gate in a second open position.

The filling gate 28 can be opened by different amounts depending on, for example, the sizes and quantities of the pills 22 being inserted into the medication container 20. For example, FIG. 2 shows the filling gate 28 in a first open position, and FIG. 3 shows the filling gate 28 in a second open position. The dimension of the opening covered by the filling gate 28 can be adjusted to account for different sized pills 22. In an example, more than one pill can be inserted at a time through the filling aperture in the top wall of the housing.

In one embodiment, both gates 28, 30 may be electronically or mechanically locked to prevent accidental opening or opening by an unauthorized person. When either of the gates 28, 30 are in their respective open positions, pills 22 can be freely inserted into or dispensed out of the interior. In some embodiments, the passage that the filling gate 28 selectively opens and closes is relatively large to allow multiple pills 22 to be inserted into the interior at a time, and the passage that the dispensing gate 30 opens and closes is relatively small so that only one pill 22 can be dispensed at a time.

In some embodiments, either or both of the gates 28, 30 may be electronically, rather than manually, opened and closed. For example, an electrical motor or solenoid, powered from an electrical power source, can operate the gate 28, 30 to move it between its closed and open positions. In some embodiments, either or both of the gates 28, 30 may be locked with a mechanical locking mechanism, such as a child safety lock in addition to or in place of the electronic lock. Such a mechanical locking mechanism may require a user push down on the appropriate gate 28, 30 and then slide the gate 28, 30 open.

In the exemplary embodiment, the dispensing gate 30 is located at one of the corners of the top surface of the housing 26 to allow the user to dispense a pill 22 into their hand in a tipping process. The filling gate 28 is located in a central area of the top surface. These gates 28, 30 may be in different locations in some embodiments. In an example embodiment, the dispensing gate 30 is locked in its closed position while the filling gate 28 is in its open position. This allows pills to be inserted into the storage volume of the housing and prevents pills that are being inserted from passing through the storage volume and exiting the dispenser through the dispensing aperture during a filling process. In an example embodiment, the filling gate 28 is locked in its closed position while the dispensing gate 30 is in its open position. This can prevent pills from falling through the filling gate 28 when the dispenser is tipped or turned upside down to dispense the pill from the dispensing aperture in the top wall of the housing, which is uncovered with the dispensing gate 30 in its open position. The dispensing process can include rotating the housing so that the top wall is facing generally downwardly with the dispensing gate 30 open so that a pill (e.g., a single pill) can pass through the dispensing aperture out of the interior of the housing 26 with the circuitry sensing the passing of the pill.

In one embodiment, the dispensing gate 30 is limited to only open by a certain amount based on a size of the pills 22 contained in the interior of the housing 26 to limit the rate that pills 22 can be dispensed. In other words, for medication containers 20 containing larger pills 22 and/or for medication containers 20 where a dose includes multiple pills 22, the dispensing gate 30 can open more than in medication containers 20 containing smaller pills 22 or containing pills 22 that are to be taken one at a time. A mechanical or electronic gate restricting device can be provided to facilitate this opening limitation.

The housing 26 further includes a display screen 32, a microphone/speaker 34, and a fingerprint sensor 36. The display screen 32 could be, for example, a liquid crystal display (LCD) screen or a light emitting display (LED) screen and may include a touch screen interface. However, any other suitable screen type may be employed. In use, the display screen 32 can display to the user a range of different information including, for example, a count of the pills 22 remaining in the medication container 20, the time of a most recent dispensing event, the time of the next scheduled dispensing event, etc. The display screen 32 may also flash, such as with colors, to provide the user with alerts. For example, a flashing green light could indicate an upcoming dispensing event according to the user's medication schedule as programmed into the medication container 20, and a flashing red light could indicate that a dispensing event is late. In some embodiments a light (such as an LED) may be provided in addition to or in place of the display screen 32 to provide alerts.

The microphone/speaker 34 may be a shared component or separate components and allows the user to communicate with the medication container 20. The microphone 34 can allow the user to audibly request either the filling gate 28 or the dispensing gate 30 to be opened or closed or to audibly request other information, e.g., the pill count or the time of the next dispensing event. The speaker 34 may allow the medication container 20 to share the requested information with the user and to provide the user with audible alerts, such as of upcoming dispensing events according to the user's medication schedule as programmed into the medication container 20. This functionality may allow users who are visually impaired to interact with the medication container 20 and better follow their medication schedules. In some embodiments, the medication container 20, through the microphone/speaker 34, may be configured to communicate with the user using artificial intelligence to improve the communication between the user and the medication container 20. In addition or alternate to the spoken audible alerts, the speaker 34 may communicate with the user via chimes, alarms, or other non-verbal audible signals.

The fingerprint sensor 36 is configured to verify a user's identity before unlocking either or both of the filling and dispensing gates 28, 30 to prevent unauthorized access to the pills 22 contained in the medication container 20. In some embodiments, a different type of biometric sensor may be employed, e.g., an iris sensor or a facial recognition sensor. In some embodiments, the medication container 20 may communicate with the external device 24 and utilize one or more biometric or password devices on the external device 24 to verify a user's identity prior to unlocking either or both of the gates 28, 30. In some embodiments, a numeric or alphanumeric keyboard may be provided on the housing to allow the user to enter a password or passcode to verify their identity.

As shown in FIG. 5, at least one guide 39 is located within the interior of the housing 26 for singulating and guiding individual pills 22 to a position aligned with the opening that is exposed by the open dispensing gate 30. The guides 39 help ensure that the user dispenses only the desired quantity of pills 22 during a dispensing operation. The guides 39 can be vertical guide walls 39 that extend within the interior between the top wall and the bottom wall of the housing 26 and narrow a width of the interior toward the exit passage opened by the dispensing gate 30. The guide walls 39 converge towards one another to singulate the pills 22 such that only a single pill 22 is aligned with the passage opened by the dispensing gate 30 at a time up until that aligned pill 20 exits the medication container 20 through the passage. The guide walls 39 can extend only in the area of the dispensing gate 30. In an example embodiment, the guide walls 39 are elongate and extend in parallel to an outer wall of the housing 26 to create an elongated channel that can guide multiple pills 22 in a one-by-many organization of at least some of the pills 22 stored in the interior of the housing 26. The pills 22 enter the channel at an open end of the generally larger volume storage in the housing 26 and exit the channel at the passage (e.g., dispensing aperture in the housing wall) that can be opened by the dispensing gate 30. The guide wall 39 will extend along one side of the passage. Sensing circuitry can be position at one or more positions along the channel to sense when a pill is present at the position of the sensing circuitry and when a pill moves past the position of the sensing circuitry in the channel. In an example, there is exit sensing circuitry at the dispensing aperture and at least one position sensing circuitry in the channel upstream from the dispensing aperture.

Referring now to FIGS. 6 and 7, an alternate embodiment of the medication container 120 is generally shown with like numerals, separated by a prefix of "1," identifying like components with the first exemplary embodiment described above. In this embodiment, the gates 128, 130 have living hinges for opening upwardly to expose the respective openings, whereas the gates of the first embodiment described above slide between the open and closed positions. Each gate 128, 130 is provided with a tab to assist the user in opening the gate 128, 130. In this embodiment, the filling gate 128 is located in a corner of the housing 126. In some embodiments, the medication container may be provided with differently configured gates, e.g., one sliding gate and one gate with a living hinge.

Figure 8:
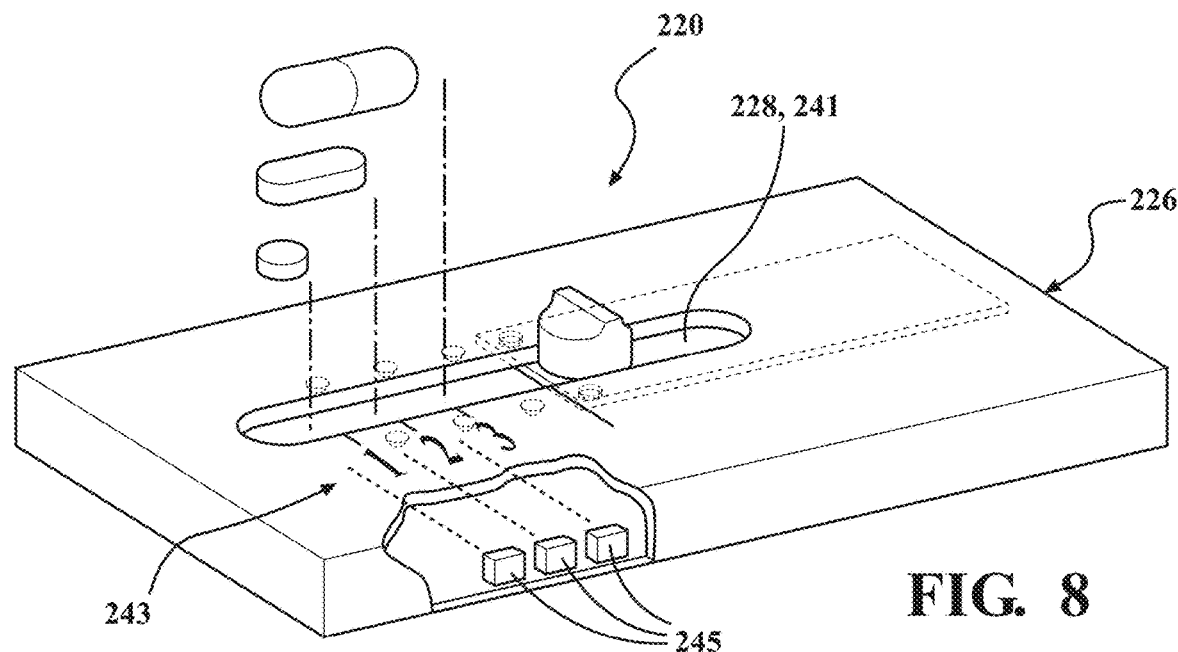
FIG. 8 is a perspective and elevation view of yet another embodiment of the medication container.

Referring now to FIG. 8, yet another embodiment of the medication container 220 is shown with like numerals, separated by a prefix of "2" identifying like components with the embodiments described above. In this embodiment, the filling gate 228 has the form of a sliding door 241. The sliding door 241 can move from a closed position enclosing the interior of the medication container 220 to an open position at which pills can enter the interior. The sliding door 241 is shown at the open position with the reference numeral 241' and with the broken lines. The multiple positions are shown at 243 with indicia "1," "2," and "3." At the first position "1," the opening created by the sliding door 241 is the smallest and is used for dispensing smaller pills. In an example embodiment, at least one first sensor (such as a light or infrared [IR] sensor) is positioned at the opening defined by the position "1" of the sliding door 241. In an example embodiment, at least one second sensor (such as a light or IR sensor) is positioned at the extended opening defined by position "2" of the sliding door 241. In an example embodiment, at least one third sensor (such as a light or IR sensor) is positioned at the opening defined by position "3" of the door 241. In the third position "3," all three sensors are activated. The sensors can sense when pills are being placed into the medication container 220 or when pills are dispensed therefrom. At least one of the sensors can trigger a scale, which is discussed in further detail below, to weigh the contents of pills within the interior of the medication container 220. The sensors can also trigger communication with external devices, e.g., a remote server or a mobile phone app. The sliding door 241 can be mounted in guideways formed into the top wall of the housing 26 to allow the movement of the sliding door 241 in its elongate direction. There can be ball and detent mechanisms to assist the user in engaging the sliding door 241 and holding it in any of the "1," "2," or "3" positions. In an example embodiment, the sliding door 241 when in any of the open positions interferes with the opening of the dispensing gate 230 to hold the dispensing gate 230 closed during the filling process. In another embodiment, the sliding door can have a shingle-like construction with multiple individual pieces (for example, 3 or 4 pieces) that can be extended to close off the filling opening and that can fold together with one another to expose the filling opening. The pieces can fold together to allow a variable opening with infinite number of sizes. The gate pieces can also stack one under the other as needed to vary the opening size into which the pills can be inserted.

A circuit board substrate can be mounted inside the interior of the medication container 220 and in electrical communication with the sensors to provide the functions described herein.

Referring now to FIG. 14, an alternate embodiment of the housing 326 is generally shown with like numerals, separated by a prefix of "3," identifying like components with the embodiments described above. In this embodiment, a pair of dividing walls 337 extend across the interior of the housing 326 to divide the interior into four separate chambers, which can contain different types of pills. The housing 326 further includes four separate dispensing gates 430 that can individually open and close to allow pills to be inserted into or removed from any of the chambers. In this embodiment, the four chambers are equal in size. However, in some embodiments, the dividing walls 337 can be located such that the chambers have different sizes. In some embodiments, the housing may only include a single dividing wall or may include three or more dividing walls such that the interior of the housing can be divided into any suitable number of separate chambers. By allowing different types of pills to be stored in the medication container 320 and allowing the medication container 320 to monitor dispending events for each of these different types of pills, the user's overall medication compliance can be improved. This embodiment can also allow the individual detection of medications in the respective passage. In some embodiments, the housing may include fewer dispensing gates than chambers with each dispensing gate being configured to open one or more of the chambers.

Figure 9:
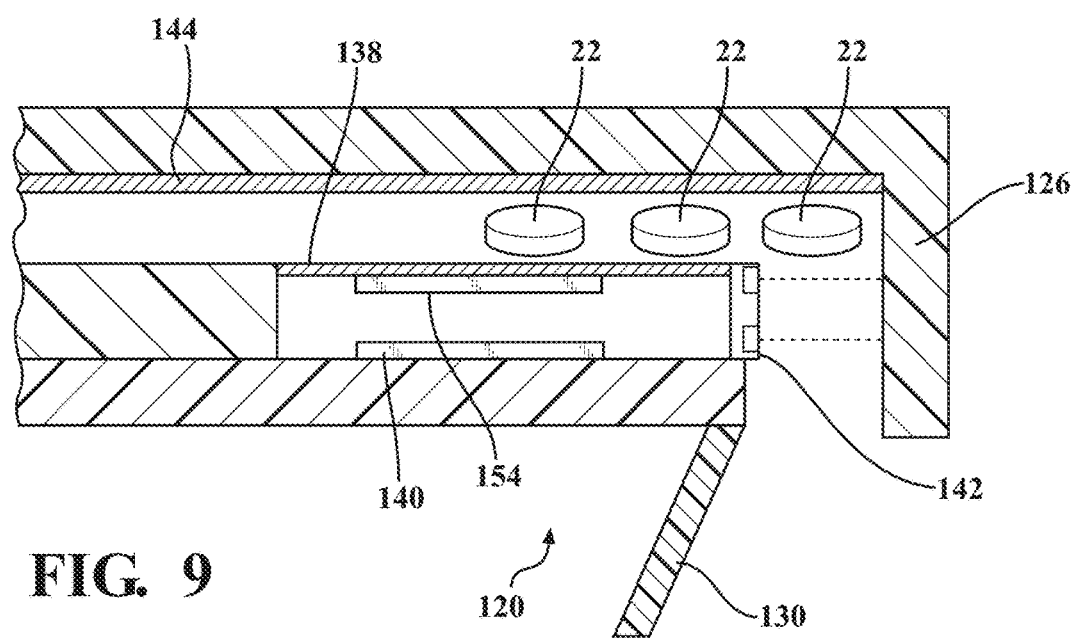
FIG. 9 is a fragmentary and cross-sectional view of the medication container of FIG. 6 in an inverted orientation to dispense a pill through the dispensing opening.
Figure 13:
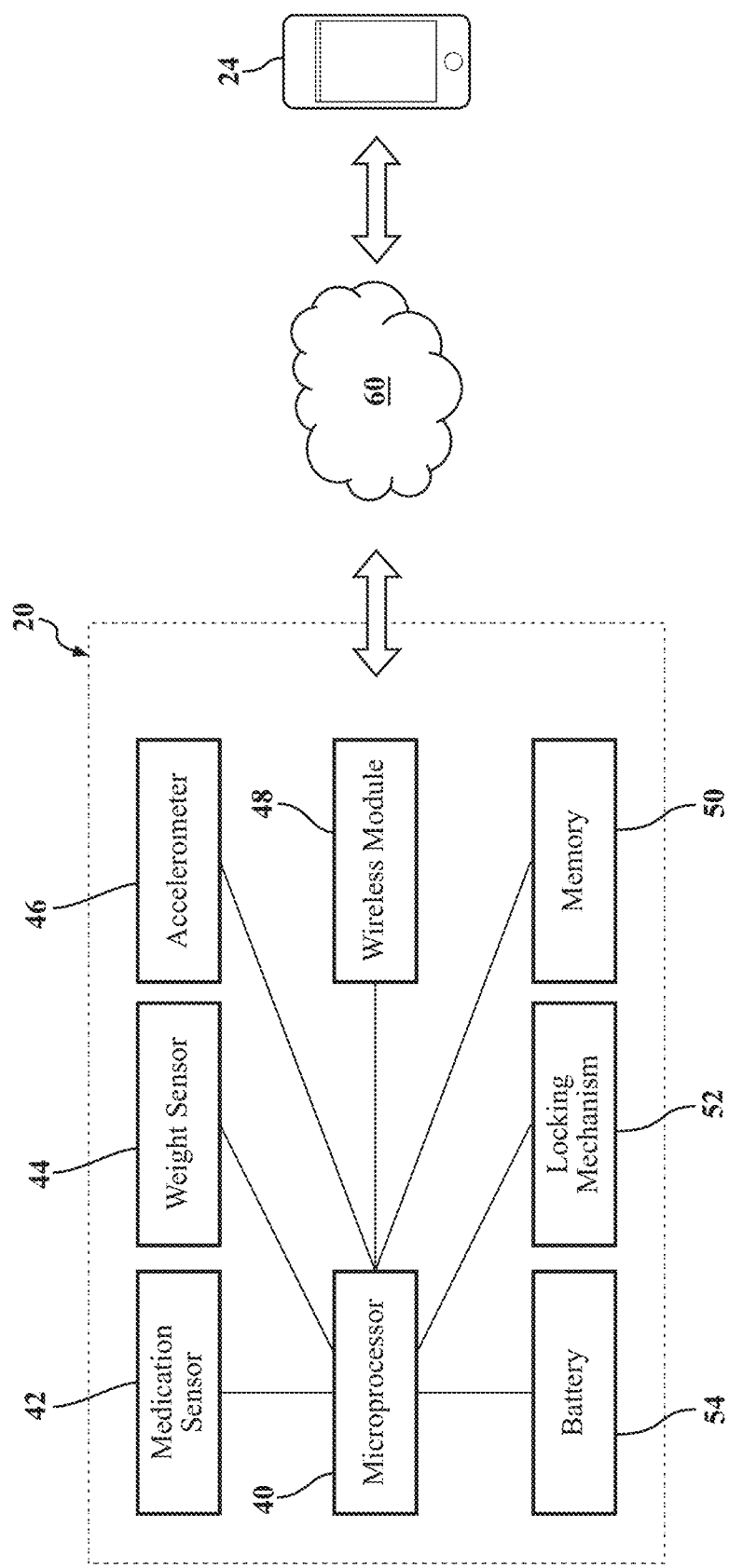
FIG. 13 is a schematic view of the medication container and showing it in communication with an external device.

Referring now to FIGS. 9 and 13, an electronics substrate 38, such as a printed circuit board (PCB), is positioned within the interior of the housing 26 and is in electrical communication with the electrical components of the medication container 20. In addition to the devices discussed above, the electrical components may include one or more of processor(s) 40 (such as a microprocessor), medication sensor(s) 42, weight sensor(s) 44, accelerometer(s) 46, a wireless module(s) 48, memory/memories 50, locking mechanism(s) 52, and battery/batteries 54. These different electrical components could be separate from or packaged along with one another.

In this embodiment, some of the electronic components are positioned within an electronics chamber 55 that is sealed against the top wall of the housing 126 to assist in preventing dust and the like from entering the chamber 55 and interfering with the electronics contained therein. In some embodiments, the electronics chamber 55 can either be pre-formed into the housing 126 and then the electronic components can be inserted into it or the electronics chamber 55 can be pre-formed and can be inserted into the interior of the housing 126 with the electronics already contained therein as a pre-assembled unit.

In this embodiment, the electronics chamber 55 is positioned adjacent the dispensing opening, and the medication sensors 42 are located at the dispensing opening for detecting pills 22 traveling either out of the receptacle 22 in a contactless manner, i.e., the pills 22 do not have to touch the medication sensors 42 for the medication sensors 42 to be triggered and for the medication container 20 to register the event as a dispensing event. Thus, the medication sensors 42 do not include any moving parts that require contact from the pills 22 to detect dispensing. In one embodiment, each medication sensor 42 includes an emitter (e.g., a light source 56) and a detector 58 for detecting reflected light from the light source 56. The light source 56 is a light emitting diode (LED), which is configured to emit light in the infrared wavelength band, in an example embodiment. In an example embodiment, the wavelength of light emitted from the light source 56 is greater than six hundred and twenty-two nanometers (622 nm). However, other types of light sources that emit light with different wavelengths may alternately be employed.

Figure 10:
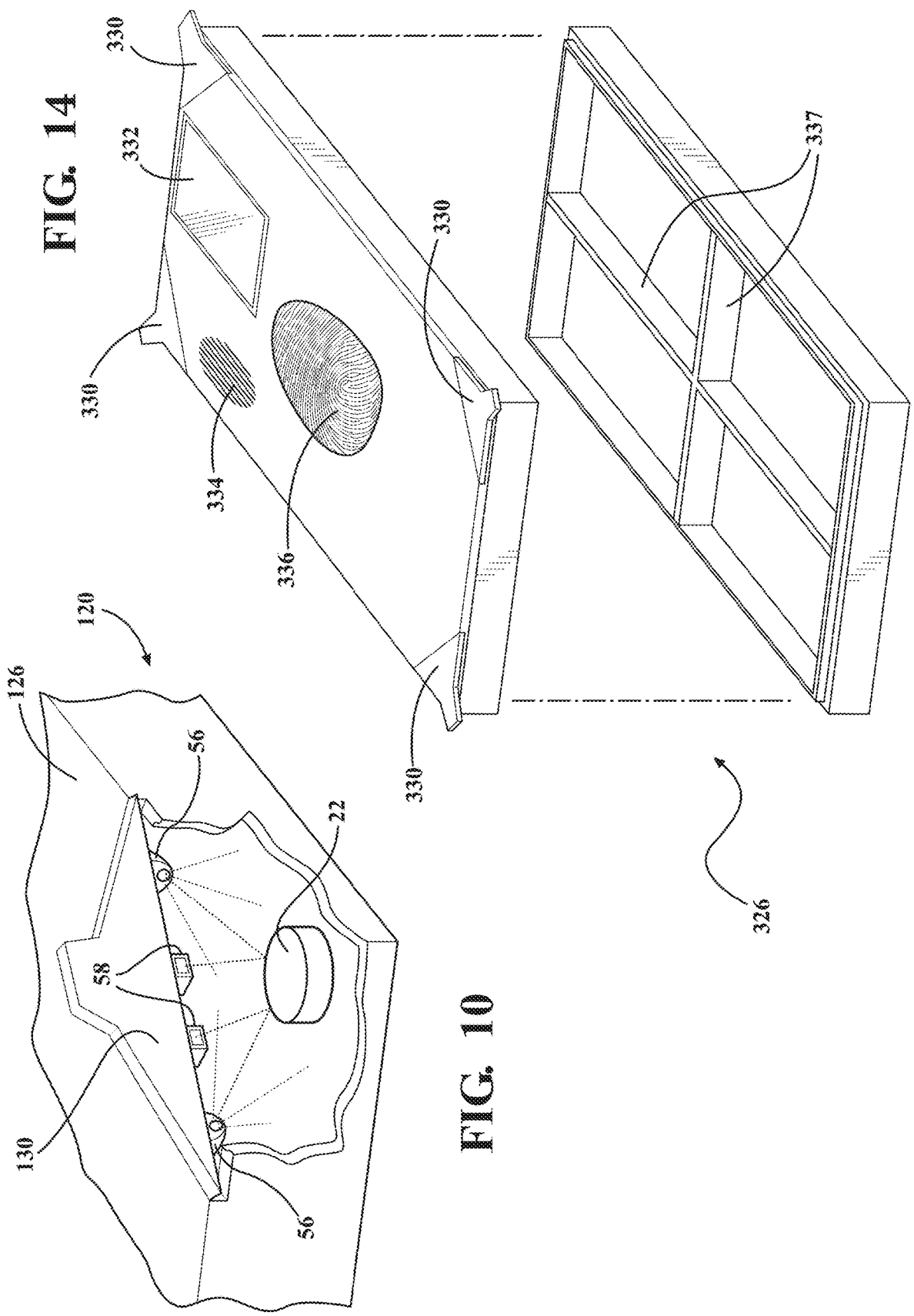
FIG. 10 is an enlarged view of the medication container of FIG. 6 and showing a pill being located in the dispensing opening and being detected by a plurality of medication sensors in the dispensing opening.

As shown in FIG. 10, each light source 156 is directed to project light in a direction towards an opposite wall of the dispensing opening, e.g., through a lens or collimator, which can be mounted to an inwardly, opening in facing wall of the dispensing opening. Each light detector 158 can be a photodiode, which responds to a change in light, such as by generating a voltage or another signal, when light is projected on a surface of the photodiode. The light detector 158 can communicate this voltage (or other signal) to the microprocessor 40 (shown schematically in FIG. 13), which can use this information to determine if a dispensing event occurred. Depending on the type of pills 22 (specifically, their color, reflectivity, and transparency) contained in the medication container 120, the opposite wall of the dispensing opening may be white, black, reflective, or colored such that the light detectors 158 generate a baseline voltage when the dispensing opening is empty.

As shown in FIG. 9, in this embodiment, at each dispensing opening, each medication sensor 142 is configured to emit two vertically spaced apart beams of light across the dispensing passage and detect the reflections of those light beams off of either the opposite wall of the dispensing passage or off of a pill 22. The beams of light can be spaced apart from one another by a distance that is greater than a major dimension of the pills 22 contained in the medication container 20. The medication sensor 142 is in electrical communication with the microprocessor 140 for communicating all events where the beams of light are broken to the microprocessor 140. In another embodiment, the sensors could be located at other locations and project light in different directions to detect pills being dispensed from the medication container in different directions or to detect pills that are immediately adjacent to one another (side-by-side). In one such embodiment, the medication sensors could be arranged in an L-shaped pattern. In some embodiments, one or more of the medication sensors can be located at the opening of the top wall and one or more medication sensors can be positioned upstream of the singulator. Together, the medication sensors can ensure an accurate count of medications being dispensed.

Figure 11:
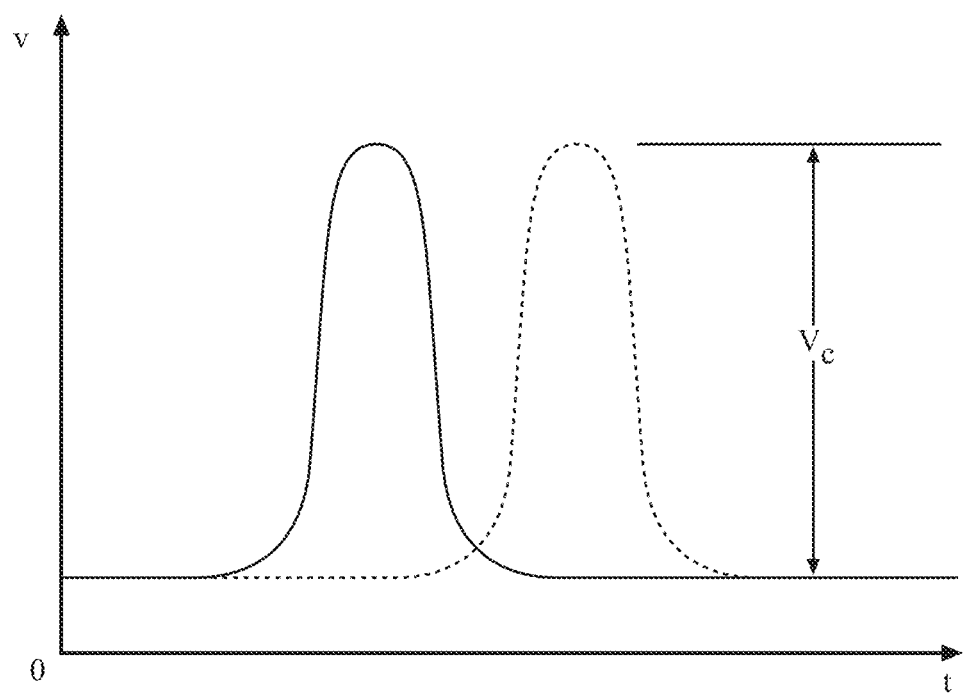
FIG. 11 is a plot illustrating the voltages produced by a pair of vertically spaced medication sensors as a pill passes through the dispensing opening.

In operation, when a pill 22 travels through the dispensing opening out of the medication container 20, some of the light emitted by one of a first light source (the upper light source according to the orientation of the housing 26 in FIG. 9) reflects off of the pill 22 and back to one of the upper detectors 58 (again with reference to the orientation of FIG. 9), thereby changing the voltage produced by that light detector 58. The magnitude of this voltage change $V_C$ will depend, inter alia, on the baseline voltage when the dispensing opening is empty and the color and reflectivity of the pill 22. After the pill has passed the light emitted by the upper light source 56, the voltage generated by the upper voltage detector 58 returns to the baseline voltage. The solid line in FIG. 11 illustrates a plot of the voltage generated by the upper light detector 58 as a pill 22 is travelling through the dispensing opening. Next, a similar voltage path is generated by the lower light detector 58 as the pill 22 passes the light emitted by the lower light source 56. The dashed line in FIG. 11 illustrates a plot of the voltage generated by the lower light detector 58 as the pill 22 is travelling through the dispensing opening. As can be seen, the upper and lower light detectors 58 produce similar voltage patterns but with the lower light detector's voltage pattern lagging behind the upper light detector's voltage pattern by the time it takes for the pill to travel from the upper beam of light to the lower beam of light. A reverse order of the voltage patterns (with the dashed line leading the solid line) will indicate an addition, rather than a dispensing, operation.

The microprocessor 40 is pre-programmed to recognize the certain voltage changes $V_C$ (see FIG. 11) as being associated with the pills 22 of the medication container 20 and to program into the memory 50 data associated with each event in which that voltage change $V_C$ is detected. In an embodiment, the microprocessor 40 may be configured to recognize a voltage change $V_C$ of 325±25 mV as being associated with one type of pill 22 and to recognize a voltage change $V_C$ of 250±25 mV as being associated with a different type of pill 22. In other embodiments, the voltage change $V_C$ may be a negative value, i.e., the voltage at the light detector 58 decreases when the pill 22 passes travels through the dispensing opening. For example, in one embodiment, the microprocessor 40 may be configured to recognize a voltage change $V_C$ of −175±25 mV as being associated with a particular type of pill 22. In either scenario where the voltage change $V_C$ is either positive or negative, the microprocessor 40 interprets such an event as a positive confirmation that a pill 22 has passed into or out of the medication container 20 (depending on which of the light detectors experiences the voltage change first) and records the event into the memory 50.

Figure 12:
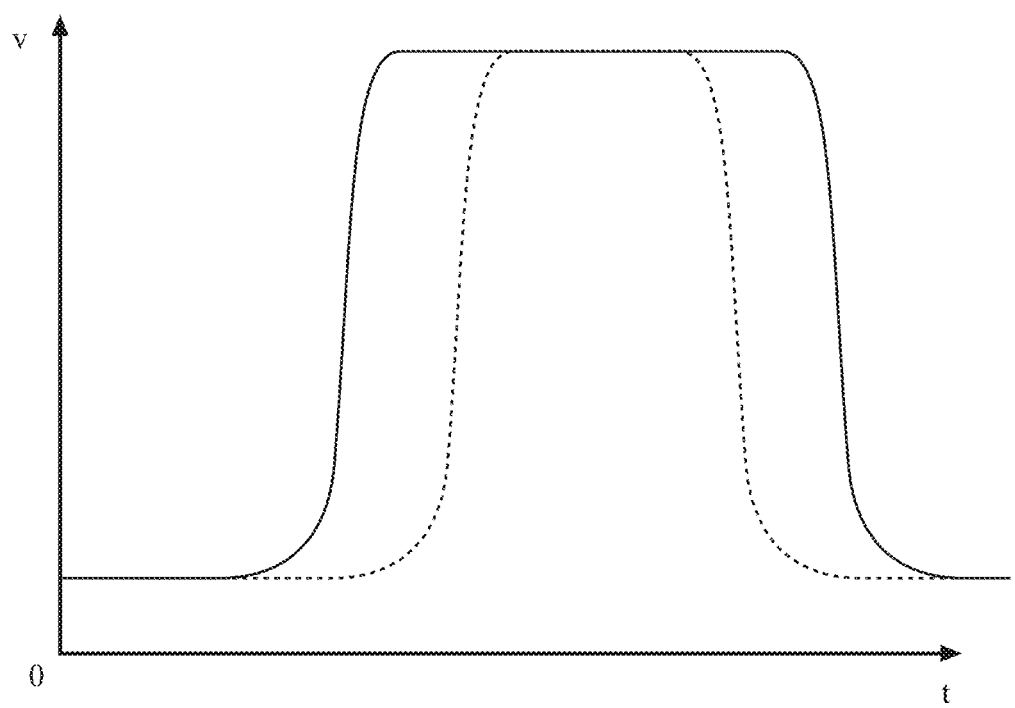
FIG. 12 is a plot illustrating the voltages produced by a pair of vertically spaced medication sensors as a foreign object is inserted into the medication opening.

If both of the beams of light are broken simultaneously, then the microprocessor interprets this event as either multiple pills 22 being dispensed at the same time or that something else (other than the pills 22) has been inserted into the dispensing opening. Thus, the microprocessor 40 may be able to differentiate a dispensing event from a false dispensing event, e.g., the user inserting their finger into the dispensing opening. FIG. 12 depicts a plot showing the voltages generated by the vertically spaced apart light detectors 158 during an event where something other than a pill is inserted into the dispensing opening. As shown with a solid line the voltage increases for a first light sensor (the one nearest the gate 130), and as shown with a dashed line, the voltage later increases for a second light sensor (the one nearest the interior). The voltage then decreases first for the second light detector and then for the first light detector.

In some embodiments, the medication container 20 may periodically recalibrate itself to establish a new baseline voltage, i.e., the voltage produced by the light detector of the medication sensor 42 when the dispensing opening is empty. The recalibration process may be to improve performance of the cap assembly because dust or other particles can settle on the light detector or a reflective surface on the opposite side of the dispensing opening from the light detector, thereby and impacting the amount of light that is emitted and/or received by the light detector when the dispensing opening is empty and altering the baseline voltage produced by the light detector. The calibration process includes activating the medication sensor 42 when the dispensing opening is empty and measuring the voltage produced by the light detector 58. Once a generally constant voltage is measured for a predetermined period of time, (for example, two seconds) without any substantial voltage changes, such as voltage spike, this constant voltage is set as the new baseline voltage. The voltage change $V_C$ measurement used to determine if an object in the dispensing opening is a pill 22 or something else, does not have to be adjusted over time.

The data that is saved into the memory 50 following a dispensing event preferably includes a time stamp and a quantity of pills 22 detected and dispensed out of the dispensing opening. Other data that may be saved into the memory 40 includes a temperature at the time of dispensing (if the medication container 20 further includes a temperature sensor) and remaining battery capacity information. The fact that the medication container 20 only records a dispensing event when the correct voltage change $V_C$ is detected reduces false positives and improves accuracy of the data saved into the memory 50. The microprocessor 40 may also be configured to record data into the memory 40 when non-dispensing events occur, such as if the dispensing gate 30 is opened but no pill 22 is detected in the dispensing opening. In one embodiment, data is recorded onto the memory 50 each time the dispensing gate 30 is opened for more than a predetermined time threshold (such as two seconds).

In another embodiment, the medication sensors 42 are photoreflective diffuse sensors that are configured to sense a break in a path of light from the light source (also known as a sender or emitter) to the light detector (also known as a receiver). Specifically, in an example embodiment, a far wall of the dispensing opening opposite of the medication sensors 42 can be coated with a highly reflective coating such that, in a resting condition with the dispensing opening being empty, a beam of light emitted from the light source 56 reflects off of the reflective coating and is sensed by a phototransistor of the light detector. In another example, the base line reading is the light reflecting off the opposite wall and returning to the light detector 58; the reflector is the uncoated polymer that forms the opposite wall. In this embodiment, the opposite wall can be a smoothed polymer. When a pill 22 travels through the dispensing opening either into or out of the interior of the housing 26, one or more of the medication sensors 42 are triggered by a breakage of the path of this beam of light. In an example embodiment, the medication sensor 42 can work by ambient light in the dispensing opening, e.g., detecting a change in the light sensed reflected in the dispensing opening without its own light source to illuminate the dispensing opening. Such an event with either of the medication sensors 42 is interpreted by the microprocessor 40 as a positive confirmation that a pill 22 has either passed into or out of the interior of the housing 26. The number of medication sensors 42 may be dictated by the sizes and shapes of the pills 22 that will be contained in the medication container 20 with more medication sensors 42 being preferred for smaller pills 22 to ensure that any pills 22 travelling through the dispensing opening break at least one of the light beams. The light beams emitted by the light sources 56 may be in the infrared range such that the light beams are invisible to the human eye. In another embodiment, the medication sensors 42 are of the type that are capable of sensing the breakage of a beam of light from the light source 56 without the need for the reflective coating on the far wall of the passage 46.

In yet another embodiment, the medication sensors 42 include imagers (for example, cameras), which are configured to capture image of the pills 22 traveling through the dispensing opening and communicate those images to the microprocessor 40. The microprocessor 40 can then automatically confirm that the pill 22 is the correct type of pill 22 by scanning the image for a size, shape, and color match and/or for an etching or other indicia on the pill 22. This improves medication compliance by positively confirming that each dispensing event recorded to the memory 50 is for the correct pill 22 and not an error. The image may be stored in the memory 50 of the medication container 20 and ultimately uploaded to the external device 26 via the wireless module 48, as discussed in further detail below.

In another example embodiment, the medication sensors 42 include signal emitters 56 (in place of light sources), and the detectors 58 can detect the signals. The signal emitters 56 can emit an ultrasonic signal that is sensed by the detectors 58. In an example, the emitters are radio frequency (RF) emitters and the detectors detect change in the emitted signal. The associated circuitry can detect the presence of a pill 22 in the dispensing opening by a phase shift in the signal or a time shift in the signal received versus the signal emitted.

In an example embodiment, the medication sensors 42 can include detection circuitry to detect when a pill 22 passes into the dispensing opening. The detection circuitry can detect the change in light, sound source, RF signal, or the like to determine passing of one or more pills 22 past the medication sensors 42.

In yet another example embodiment, each medication sensor 42 includes a camera and a light source, and the opposite wall of the dispensing opening has the at least one concave mirror. In operation, the light source projects light against the concave mirror, which reflects and focuses the light onto the camera. The camera takes images of any pills 22 travelling through the dispensing opening to detect pills 22 travelling through the dispensing opening. The images captured by the camera can be analyzed by the microprocessor 40 to confirm that the pills 22 contained therein are correct.

The accelerometer 46 is in electrical communication with the microprocessor 40 and is configured to sense movement of the medication container 20, such as opening or closing of one of the gates 28, 30 or a tilting of the medication container 20. In the first embodiment, the microprocessor 40 is configured to put the electrical components in a low power (sleep) mode after a predetermined time wherein the accelerometer 46 senses no or little movement, thus preserving power and extending battery life. For example, the microprocessor 40 could be configured to reduce or cut power to all of the electronic components in the medication container 20 except itself and the accelerometer 46 when the accelerometer 46 fails to sense any movement for a half-minute, one minute, two minutes, three minutes or the like. When the medication container 20 is in the low power mode, the microprocessor 40 is configured to immediately activate the electrical components in response to the accelerometer 46 detecting movement and providing an "ON" signal to the microprocessor 40.

In an embodiment, the accelerometer 46 also is configured to sense an orientation of the medication container 20 so that the microprocessor 40 can determine whether a trigger event by the medication sensors 42 is the travel of a pill 22 into or out of the interior of the housing 26. Specifically, if the accelerometer 46 senses that the medication container 20 is upside down or is angled downwardly at the time when one or more of the medication sensors 42 are triggered, then this indicates that a pill 22 has been poured out of the housing 26, and the microprocessor 40 records the event in the memory 50 as a pill 22 leaving the medication container 20. Conversely, if the accelerometer 46 senses that the medication container 20 is in an upright or an upwardly angled orientation at the time when one or more of the medication sensors 42 are triggered, then the microprocessor 40 records the event as a pill 22 being inserted into the housing 26.

In an example embodiment, the circuitry, e.g., including the microprocessor 40, the medication sensors 42 and the accelerometer 46, can be trained to sense the dispensing movements of housing 26. Users may have individual, personal movements to dispense a pill from the dispenser. The dispenser circuitry can indicate to the user to perform a dispensing act and sense the motion of the housing. The dispenser circuitry can indicate to the user to perform a pill insertion act and sense the motion of the housing. This can be repeated until the motions are sensed and repeated within a margin of error. These motions ca be used to confirm the sensed insertion of pills and the dispensing of pills, e.g., in conjunction with the sensor circuitry.

The wireless module 48 is configured to transmit and receive data with the external device 24 (such as a smart phone, a tablet, a personal computer, a smart watch, a dedicated unit, server, or any suitable type of electronic device) either directly or via the internet 60. The wireless module 48 could be configured to communicate with the external device 24 via one or more of Bluetooth®, WiFi®, near field communications (NFC®), cellular communication, or any suitable wireless protocol or protocols. In an embodiment, the wireless module 48 is configured to communicate with the external device 24 via cellular communication channels, thereby eliminating the need for the user to pair or otherwise set up direct communication between the medication container 20 and the external device 24 and allowing the data to be uploaded to the external device 24 even when the external device 24 is not in the proximity of the medication container 20. Depending on the region, the wireless module 48 may be configured to communicate using Narrowband IoT and/or LTE-M technology. The external device 24 may also be a smart speaker that can allow a user to check if they have already taken their pill(s) 22 or which can remind the user when to take their pill(s) 22 according to the schedule. The external device 24 may further be a cloud accessible storage device that can store all of the data generated by the medication container 20 as a backup in the event that the medication container 20 is lost or damaged.

The wireless module 48 and the external device 24 can be configured to encrypt and verify all data communication therebetween, regardless of the form of wireless communication. The memory 50 can store at least the data that is to be transferred to the external device 24 so that this data is not lost if pills 24 are either added to or removed from the medication container 20 when the wireless module 48 is not in active communication with the external device 24. In other words, when the wireless module 48 is not actively in communication with the external device 24, the medication container 20 can operate as a stand-alone unit, which stores data internally until that data can be uploaded to the external device 24. The memory 50 may also contain data for an updatable medication count for the medication container 20. The medication count may be initially set by a pharmacy that fills the medication container 20 or may be set by the user. The memory 50 is preferably of the non-volatile type such that the data stored thereon is not lost in the event of a power failure.

The weight sensor 44 is configured to automatically determine the pill count within the interior of the housing 26. In the embodiment of FIG. 9, the weight sensor 44 includes a false floor and one or more compressible elements that compress as a function of the mass of pills 22 in the interior when the housing 26 is in a right-side-up orientation, i.e., the opposite orientation of what is shown in FIG. 9. Using a known mass of each pill 22 and the sensed mass of all of the pills 22, the microprocessor 40 is able to determine the pill count.

The battery 54 is mounted on the electronics substrate 38 and is electrically connected with all of the electronic components to power these components. The battery 54 could be designed to be easily replaced to allow for re-use of the medication container 20 or the medication container 20 could include a charging port which allows the battery 54 to be recharged. The battery 54 could also be configured for wireless charging.

The locking mechanism 52 or mechanisms may include one or more solenoids and are configured to selectively lock and unlock the filling and dispensing gates 28, 30. As discussed above, the microprocessor 40 can be configured to control the locking mechanism 52 upon a positive confirmation of a user's identification.

The medication container 20 and/or the external device 24 may also be configured to automatically alert a user when it is time for the user to take a dose of the pills 22. In some embodiments, a medication schedule is programmed into the memory 50, and the microprocessor 40 is configured to alert the user each time the user is to take a dose of the pills 22 according to the medication schedule. The medication schedule can be changed by a user and/or could be remotely changed by either the pharmacy or a doctor via the external device 24. The alert could be, for example, a notification displayed on or broadcast by either or both of the medication container 20 and the external device 24. In the exemplary embodiment, the medication container further includes an alert means in the form of the display screen 32 and/or a light, which can visually alert the user. For example, the alert could be the light changing colors or flashing at different rhythms. The display screen 32 and/or the light may also communicate other messages to the user, such as when the battery 54 needs to be recharged or replaced.

As discussed above, the external device 24 and/or the memory 50 is/are programmed to maintain a continuously updated record of each positive confirmation of pill(s) 22 leaving or entering the medication container through either of the filling and dispensing openings and communicate that record when prompted by the user or a medical provider (such as a doctor). Thus, in the event that a user is unsure, the user can check the record to determine if the pill 22 was removed. The medical provider may then use the record to determine if the user is properly following a prescribed medication schedule. This improves medication adherence by eliminating doubt for both the user and the medical provider without the user having to take any additional steps, such as writing down the time each pill 22 was taken. The external device 24 may include an app that can also communicate with a remote, cloud-based database via internet protocols, which maintains a copy of the medication count and the records. This advantageously allows the user, the medical provider, and/or a pharmacy to access the data from different devices and also ensures that the data is not lost if the user loses or otherwise damages the medication container 20 or the external device 24.

Systems and methods described herein can determine whether and/or when a patient is taking the prescribed pills 22. The cap assembly 20 or the external device 24 can provide, when appropriate, reminders and/or alerts to the patient or patient representative to improve adherence to a medication regimen.

In some embodiments, the medication container 20 includes an interface that can alert the user to environmental conditions that may compromise the integrity of the pills 22, e.g., temperature sensors determining that ambient temperature has exceeded a certain temperature, that a thermal budget has been used, or that the interior has exceeded a predetermined moisture level. The circuitry in the medication container 20, through its communications circuitry can electronically communicate with prescribing doctor's devices, pharmacy devices, insurance companies, pharmacy benefits management devices, and other parties that may be interested in prescription practices and adherence.

The external device 24 may further include an app or computer program that is configured to communicate with the medication container 20 to allow the user to interact with the medication container 20. The app may be able to do any combination of the following functions: history tracking of medication events; provide reminders, such as through text messaging, E-mail, or through a phone call; provide caregiver support; select, download, and delete data; allow the user to provide feedback after each medication take; allow the user to request a refill; control a rewards program which gives the user rewards for following a medication schedule; and warn the patient when a medication schedule attempts to pair incompatible medications. Further, the app may work either when the external device 24 is or is not in communication with the medication container 20 and may allow the user to manually enter other medication taking events, such as if the medication container 20 is not working or such as for other medications than those contained in the medication container 20. The app may further integrate with an existing electronic health records (HER) platform to automatically populate those records with a medication history. This may reduce the number of steps needed by both the patient and the providers to set up a medication adherence program and limit mistakes from patients who self-enter their medication. In one embodiment, the external device 24 may be configured to pair with the medication container 20 by scanning a code (such as a quick response [QR] code) on the medication container 20.

The schedule programmed into the memory 50 of the medication container 20 may be a single day schedule, a weekly schedule, or a monthly schedule. The medication container 20 may also be configured to operate without any schedule programmed therein. In this condition, any dosage event recorded to the memory 50 as being on time except if that dosage event occurs within a predetermined time (for example, one or two hours) of another dosage event. In that case, the second dosage event is recorded to the memory 50 as being an extra take.

In an embodiment, the medication container 20 may include one or more gate limiters that are configured to limit the amount that the gates 28, 30 can open based on the size of the pills 22 contained in the interior of the housing 26. In one embodiment, the gate limiter can be a non-electronic device that is set to allow the respective gate 28, 30 to open by a predetermined amount in a pharmaceutical setting based on the type of pill 22 that is to be included in the medication container 20. In another embodiment, the gate limiter can be electronic including one or more solenoids and can be adjustable to change the amount that the gate 28, 30 can open.

Figure 15:
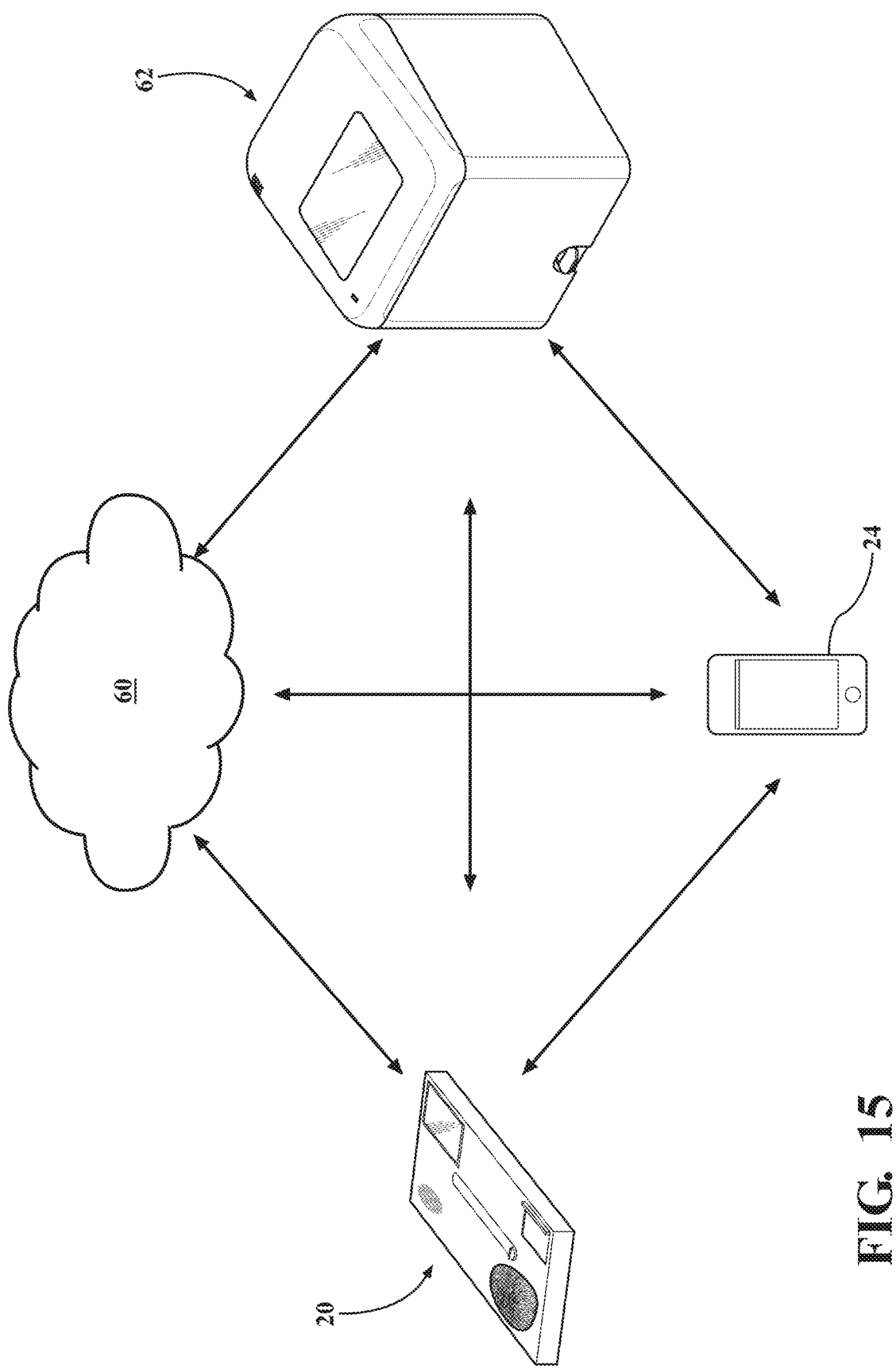
FIG. 15 is a schematic view illustrating the communication between a medication container, an external device, and a dispensing device.

Referring now to FIG. 15, the medication container 20 may be configured to communicate with a medication dispenser 62. Such a medication dispenser 62 can be a personal countertop device that contains one or more type of medication and is programmed to automatically dispense pills according to a programmed medication schedule or upon receiving a demand for one or more pills. If a user is going to be away from the medication dispenser 62 for a period of time (for example, the user is leaving their house for one or more days), the user can dispense a sufficient quantity of pills to last for the time they are away from the medication dispenser 62 and insert those pills into the medication container 20. For the embodiments where the medication container 20 includes multiple chambers, different types of pills can be dispensed from the medication dispenser and put into the different chambers of the medication container 20. The medication dispenser 62 can then automatically communicate with the medication container 20 via wireless protocols to program the user's medication schedule into the memory of the medication container 20 and/or to store a medication count of the pills dispensed by the medication dispenser 62 into the medication container 20. This communication could be direct, via the internet, or via the external device 24. Once programmed into the memory of the medication container 20, the medication container 20 can automatically alert the user (such as with the display screen, the light, or the speaker) for each dosing event and can alert the user when a medication count in the medication container 20 falls below a predetermined threshold.

Both the medication dispenser 62 and the medication container 20 can communicate with a database that may be located, for example, on the external device or on a cloud-based server and may be accessible by a third party (such as a medical care provider, a pharmacy, or a pharmacy benefit manager) to allow the user or the third party to monitor the user's medication adherence, whether the user is dispensing the pills from the medication dispenser 62 or the medication container 20. More specifically, either a dispensing event by the medication dispenser 62 or a dispensing event by the medication container 20 can be recorded to a database that can be accessed by various parties using various devices, including the external device 24.

In various embodiments, the medications can be non-liquid medications such as individualized dose medications or other individualized solids. In various descriptions here, the term "pill" is used to simplify the description and any example that uses the term pill can also be used with non-liquid solids, e.g., medications. It will be further understood that the individualized dose medications can contain liquid therein, e.g., within gel capsules. The individual dose medications can be individually counted when they are dispensed from the receptacle past the medication sensor aligned with the passage. The sensors can also determine that a mis-dispense has occurred, e.g., more than a set number of individualized dose medications being d. The medication, as in some embodiments, is a small, solid dosage form of a globular, ovoid, spheroid, or lenticular shape, containing one or more medical substances, supplemental substances, spices, or combinations thereof. The container and the cap are adapted to store these forms and prevent entry of environment into the interior of the medication container when closed by the cap assembly. The medication container is adapted to hold a plurality of the forms, e.g., ten, twenty, thirty, sixty, ninety, or multiples thereof.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

The word "example" is used herein to mean serving as an example, instance, or illustration. Any aspect or design described herein as "example" is not necessarily to be construed as preferred or advantageous over other aspects or designs. Rather, use of the word "example" is intended to present concepts in a concrete fashion. As used in this application, the term "or" is intended to mean an inclusive "or" rather than an exclusive "or." That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form. Moreover, use of the term "an implementation" or "one implementation" throughout is not intended to mean the same embodiment or implementation unless described as such.

Implementations of the systems, algorithms, methods, instructions, etc., described herein may be realized in hardware, software, or any combination thereof. The hardware may include, for example, computers, intellectual property (IP) cores, application-specific integrated circuits (ASICs), programmable logic arrays, optical processors, programmable logic controllers, microcode, microcontrollers, servers, microprocessors, digital signal processors, or any other suitable circuit. In the claims, the term "processor" should be understood as encompassing any of the foregoing hardware, either singly or in combination. The terms "signal" and "data" are used interchangeably.

As used herein, the term module may include a packaged functional hardware unit designed for use with other components, a set of instructions executable by a controller (e.g., a processor executing software or firmware), processing circuitry configured to perform a particular function, and a self-contained hardware or software component that interfaces with a larger system. For example, a module may include an application specific integrated circuit (ASIC), a Field Programmable Gate Array (FPGA), a circuit, digital logic circuit, an analog circuit, a combination of discrete circuits, gates, and other types of hardware or combination thereof. In other embodiments, a module may include memory that stores instructions executable by a controller to implement a feature of the module.

Further, in one aspect, for example, systems described herein may be implemented using a special purpose computer/processor may be utilized which may contain hardware for carrying out any of the methods, algorithms, or instructions described herein. The hardware may become a special purpose device when storing instructions, loading instructions, or executing instructions for the methods and/or algorithms described herein.

Further, all or a portion of implementations of the present disclosure may take the form of a computer program product accessible from, for example, a computer-usable or computer-readable medium. The program includes steps to perform, at least, portions of the methods described herein. A computer-usable or computer-readable medium may be any device that can, for example, tangibly contain, store, communicate, or transport the program for use by or in connection with any processor. The medium may be, for example, an electronic, magnetic, optical, electromagnetic, or a semiconductor device. Other suitable mediums are also available.

Various other electronic features and teachings as set forth in U.S. patent application Ser. No. 17/122,656, filed on Dec. 15, 2020, and entitled "CAP ASSEMBLY FOR A MEDICATION CONTAINER" may further be incorporated into any of the embodiments of the medication container as taught herein so long as they do not contradict the teachings herein. U.S. patent application Ser. No. 17/122,656 is herein incorporated by reference.

The above-described embodiments, implementations, and aspects have been described in order to allow easy understanding of the present disclosure and do not limit the present disclosure. On the contrary, the disclosure is intended to cover various modifications and equivalent arrangements included within the scope of the appended claims, which scope is to be accorded the broadest interpretation to encompass all such modifications and equivalent structure as is permitted under law.

What is claimed is:

1. A medication container, comprising:
    a generally card-shaped housing having an interior that is able to hold a plurality of pills;
    a first opening that is sized to allow a plurality of pills to simultaneously be inserted into the interior of the housing, a first door movable between an open position and a closed position to selectively open and close the first opening;
    a second opening that is spaced from the first opening on a same wall of the housing and is configured to only allow a single dose of pills to be dispensed from the interior of the housing at a time, a second door movable between an open position and a closed position to selectively open and close the second opening;
    electronic circuitry disposed in the interior of the housing and being configured to detect the passage of the pills through the second opening and record data pertaining to each dispensing event to a memory contained within the interior of the housing; and
    a guide including at least one guide wall which extends between the top wall and a bottom wall and is fixedly attached therebetween, said guide wall channeling the pills in the interior of the housing towards the second opening and singulates the pills such that only a single pill can be aligned with the second opening for dispensing at a time.

2. The medication container as set forth in claim 1 wherein the electronic circuitry includes at least one touchless sensor that is configured to detect the passage of pills through the second opening without contact between the at least one touchless sensor and the pills;
    wherein said touchless sensor selectively triggers a scale to weigh the pills.

3. The medication container as set forth in claim 2 wherein the at least one touchless sensor includes at least one photoreflective diffuse sensor that is configured to sense a break in a path of light from a light source to a light detector.

4. The medication container as set forth in claim 1 wherein the electronic circuitry includes a wireless module that is able to transmit the data pertaining to each dispensing event from the memory to an external device.

5. The medication container as set forth in claim 1 wherein at least one of the first door and the second door is a slidable door that can slide between the open and closed positions;
    wherein the first door has multiple positions that adjust to the size of one of said plurality of pills.

6. The medication container as set forth in claim 1 wherein at least one of the first door and the second door includes a living hinge and can pivot between the open and closed positions.

7. The medication container as set forth in claim 1 further including a door locking device in the housing that
    locks the first door and only unlocks the first door in response to a positive access approval to access the housing to add or remove a pill, and
    locks the second door and only unlocks the second door in response to sensing a positive dispensing verification that an approved person is requesting the second door to be unlocked in the housing, and
    locks both the first and second doors and only unlocks both of said doors in response to a positive approval that an approved person is requesting both the doors to be unlocked.

8. The medication container as set forth in claim 1 further including a weight sensor contained within the interior of the housing and configured to weigh the pills within the interior and also configured to transmit weight data to the electronic circuitry.

9. The medication container as set forth in claim 1, wherein the second door is a dispensing door,
    the housing further including a plurality of walls that are fixedly attached and located within the interior of the housing and dividing the housing into a plurality of chambers, and
    the housing having a plurality of dispensing doors with each dispensing door being associated with one of the chambers.

10. A medication container, comprising: a generally card-shaped housing having an interior that is able to hold a plurality of pills;
    a first opening, in a top wall of the housing, that is sized to allow a plurality of pills to simultaneously be inserted into the interior of the housing, a first door movable between an open position and a closed position to selectively open and close the first opening;
    a second opening, in the top wall of the housing, that is spaced from the first opening and is configured to only allow a single dose of pills to be dispensed from the interior of the housing at a time, a second door movable between an open position and a closed position to selectively open and close the second opening;
a non-contact pill sensor disposed at the second opening and configured to detect the dispensing of pills out of the interior volume outside of the housing; and
a guide including at least one guide wall which extends between the top wall and a bottom wall and is fixedly attached therebetween, said guide wall channeling the pills in the interior of the housing towards the second opening and singulates the pills such that only a single pill can be aligned with the second opening for dispensing at a time;
wherein the second opening is located on a corner of the top wall of the housing.

11. A medication container, comprising:
a generally card-shaped housing having an interior that is able to hold a plurality of pills;
a filling opening that is sized to allow a plurality of pills to simultaneously be inserted into the interior of the housing, a filling door movable between an open position and a closed position to selectively open and close the filling opening;
a dispensing opening that is spaced from the filling opening on the same wall of the housing and is configured to only allow a single dose of pills to be dispensed from the interior of the housing at a time, a dispensing door movable between an open position and a closed position to selectively open and close the dispensing opening;
a pair of guide walls fixedly attached and positioned within the interior of the housing and converging towards one another in a direction towards the dispensing opening for singulating the pills so that only a single dose of the pills can be aligned with the dispensing opening at a time; and
electronic circuitry disposed in the interior of the housing and being configured to detect the passage of the pills through the dispensing opening and record data pertaining to each dispensing event to a memory contained within the interior of the housing.

12. The medication container as set forth in claim 11 wherein the single dose of pills that can be aligned with the dispensing opening at a time includes only a single pill.

13. The medication container as set forth in claim 11 wherein the electronic circuitry includes at least one touchless sensor that is configured to detect the passage of pills through the dispensing opening without contact between the at least one touchless sensor and the pills;
wherein said touchless sensor selectively triggers a scale to weigh the pills.

14. The medication container as set forth in claim 13 wherein the at least one touchless sensor includes at least one photoreflective diffuse sensor that is configured to sense a break in a path of light from a light source to a light detector.

15. The medication container as set forth in claim 11 wherein the filling door is slidable between the open and closed positions and wherein the open position includes a plurality of different open positions with different areas of the filling opening being exposed.

16. The medication container as set forth in claim 11 wherein the housing further includes a plurality of walls located within the interior of the housing that are fixedly attached and dividing the housing into a plurality of chambers, and the housing has a plurality of dispensing doors with each dispensing door being associated with one of the chambers.

17. A medication container, comprising:
a generally card-shaped housing having an interior that is able to hold a plurality of pills;
a filling opening that is sized to allow a plurality of pills to simultaneously be inserted into the interior of the housing, a filling door movable between an open position and a closed position to selectively open and close the filling opening;
a dispensing opening that is spaced from the filling opening and is configured to only allow a single dose of pills to be dispensed from the interior of the housing at a time, a dispensing door movable between an open position and a closed position to selectively open and close the dispensing opening;
a guide including at least one guide wall which extends between a top wall and a bottom wall and is fixedly attached therebetween, said guide wall channeling the pills in the interior of the housing towards the dispensing opening and singulates the pills such that only a single pill can be aligned with the dispensing opening for dispensing at a time; and
electronic circuitry disposed in the interior of the housing and being configured to detect the passage of the pills through the dispensing opening and record data pertaining to each dispensing event to a memory contained within the interior of the housing;
wherein said filling door and said dispensing door are located on the top wall of the housing.

18. A medication container, comprising:
a generally card-shaped housing having a planar top and a planar bottom and having a single interior volume, a plurality of pills inserted directly and contained within the single interior volume, the interior volume having a height that is less than two times a minor dimension of the pills such that the pills cannot stack on top of one another within the interior volume;
the housing having a larger filling opening and a smaller dispensing opening on the same wall of the housing, a filling door closing the filling opening and a dispensing door closing the dispensing opening;
a pair of guide walls that are fixedly attached within the interior volume and converging towards one another in a direction towards the dispensing opening to singulate the pills within the interior volume such that only a single one of the pills can be aligned with the dispensing opening at a time;
an electronic locking mechanism selectively locks the filling door or the dispensing door in a closed position;
a biometrics sensor in electrical communication with the electronic locking mechanism and configured to only unlock the dispensing door upon a positive verification of a user;
a non-contact pill sensor disposed at the dispensing opening and configured to detect the dispensing of pills out of the interior volume outside of the housing;
a microprocessor, a memory, and a wireless module disposed within an electronics chamber within the interior volume of the housing, the microprocessor being configured to record data pertaining to dispensing events into the memory, and the wireless module being configured to communicate the data to an external device.

* * * * *